United States Patent
Palmer (10) Patent No.: US 10,980,656 B2
(45) Date of Patent: *Apr. 20, 2021

(54) REMOVABLE PEDIATRIC HIP ORTHOTIC

(71) Applicant: Jeffrey Ray Palmer, Swisher, IA (US)

(72) Inventor: Jeffrey Ray Palmer, Swisher, IA (US)

(*) Notice: Subject to any disclaimer, the term of this patent is extended or adjusted under 35 U.S.C. 154(b) by 320 days.

This patent is subject to a terminal disclaimer.

(21) Appl. No.: 15/875,462

(22) Filed: Jan. 19, 2018

(65) Prior Publication Data

US 2018/0153725 A1 Jun. 7, 2018

Related U.S. Application Data

(63) Continuation-in-part of application No. 15/262,154, filed on Sep. 12, 2016, now Pat. No. 10,561,516.

(51) Int. Cl.
*A61F 5/00* (2006.01)
*A61F 5/01* (2006.01)
*A61F 5/37* (2006.01)

(52) U.S. Cl.
CPC .......... *A61F 5/0193* (2013.01); *A61F 5/0104* (2013.01); *A61F 5/3715* (2013.01)

(58) Field of Classification Search
CPC ..................................... A61F 5/0193
USPC ......................................... 602/24
See application file for complete search history.

(56) References Cited

U.S. PATENT DOCUMENTS

| | | | | |
|---|---|---|---|---|
| 3,068,862 A | * | 12/1962 | Fuzere | A61F 5/0193 602/24 |
| 3,114,368 A | * | 12/1963 | Richmond | A61F 5/0193 602/24 |
| 3,260,259 A | * | 7/1966 | Connelly | A61F 5/0193 602/24 |
| 3,563,601 A | * | 2/1971 | Dickey | A61F 5/0193 297/466 |
| 3,834,376 A | * | 9/1974 | Thum | A61F 5/0193 602/24 |
| D266,948 S | * | 11/1982 | Kvittingen | D24/190 |

(Continued)

OTHER PUBLICATIONS

The University of Iowa Children's Hospital, Hip Spica Cast: A Guide for Patients, publication located on the University of Iowa Children's Hospital website: www.uichildrens.org; dated Feb. 2012.

(Continued)

*Primary Examiner* — Kim A Lewis
(74) *Attorney, Agent, or Firm* — Lane & Waterman LLP (57) ABSTRACT

A removable and replaceable hip orthotic that includes a back panel formed from a rigid material that supports a patient's lumbar area; a front panel formed from the rigid material that supports the patient's abdomen area and is hinged to the back panel to allow application and removal of the orthotic to the patient; a leg support that extends from the back support that includes a space that allows a patient's leg to pass through into the leg support; and straps to secure the back panel to the front panel and the leg into the leg support. The back panel includes a pair of windows with a trochanter pad movably disposed within the windows. An adjustment mechanism selectively moves the trochanter pads relative to the greater trochanter regions of the hips of the patient to apply pressure to the hip joint to prevent dislocation of the femoral head.

14 Claims, 7 Drawing Sheets

(56) References Cited

U.S. PATENT DOCUMENTS

| | | | | |
|---|---|---|---|---|
| 4,913,136 | A * | 4/1990 | Chong | A61F 5/0193 |
| | | | | 602/24 |
| 5,344,391 | A * | 9/1994 | Modglin | A61F 5/0193 |
| | | | | 602/16 |
| 5,618,264 | A * | 4/1997 | Vasquez | A61F 5/0193 |
| | | | | 602/23 |
| 2009/0216165 | A1 * | 8/2009 | Christenhusz | A61F 5/0193 |
| | | | | 602/24 |

OTHER PUBLICATIONS

The Royal Children's Hospital Melbourne, Pavlik Harness for DDH, publication located on the Royal Children's Hospital Melbourne website: www.rch.org.au/kidsinfo; dated Nov. 2010.
Cincinnati Children's Hospital Medical Center, Pavlik Harness Care, publication located on the Cincinnati Children's Hospital website: www.cincinnatichildrens.org; dated Mar. 2016.
Becker Orthopedic, Maple Leaf Orthosis, product description sheet located on the Becker Orthopedic website: www.beckerorthopedic.com; dated 2014.
International Hip Dysplasia Institute, Hip Spica Cast—Infant Hip Dysplasia, publication located on the International Hip Dysplasia Institute website: http://hipdysplasia.org.
Restorative Care of America Incorporated, Hip Orthoses, production description sheets located on the Restorative Care of America Incorporated website: www.rcai.com.

* cited by examiner

REMOVABLE PEDIATRIC HIP ORTHOTIC

CROSS-REFERENCE TO RELATED APPLICATION

This application is a continuation-in-part and claims priority to co-pending application Ser. No. 15/262,154, filed on Sep. 12, 2016, the entire disclosure of which is incorporated herein by reference.

FIELD OF THE INVENTION

The present invention relates to a hip orthotic and, more specifically, to a removable and replaceable pediatric hip orthotic.

BACKGROUND

Developmental dysplasia or dislocation of the hip (DDH) is an abnormal development of the hip joint usually identified in infants and children. In all cases of DDH, the acetabulum (the hip socket) is shallow and the ball of the femur is not stable within the hip socket. However, the severity of DDH can vary from patient to patient. To improve the condition, the hip joint is usually arranged in a position to encourage proper growth for a period of time. Frequently a cast or harness is used to maintain this prescribed position for a period of weeks or months.

The different types of restraints used to keep patients in the therapeutic position vary depending, in part, on the severity of the DDH and the age of the child. One common restraint is the spica cast. The spica cast is a typical hard-sided cast that is generally applied from the waist area to the knees of the patient in an effort to keep the hip joint immobilized in the preferred therapeutic position. Because the spica cast is cumbersome to apply while the patient is in the therapeutic position, the spica cast is typically applied while the patient is under general anesthesia. In certain procedures, pressure is applied to the greater trochanter region of the mold while the plaster cast is drying. The hardened cast will apply pressure anteriorly over the greater trochanter to prevent posterior dislocation.

Because DDH is often diagnosed and treated in patients that are young and not toilet-trained, special care must be taken when applying the spica cast to allow for diapering of the patient. However, despite the best efforts of parents and caregivers, the spica cast frequently gets soiled with urine and feces. Soiled spica casts can create skin conditions for the patient. A soiled cast that makes contact with the skin can cause rapid skin breakdown leading to discomfort, painful sores, rashes, and other skin conditions. Because the spica cast is generally worn for 6 to 12 weeks at a time, the child must either be left in a soiled cast which may cause skin irritation or have a new cast applied which may require general anesthetic. It is desirable therefore, to have a cast that can be removed and cleaned or replaced when soiled but that does not require anesthesia or significant discomfort to the patient during removal and re-application. It is further desirable to provide a removable cast that can apply anterior pressure to the greater trochanter to prevent posterior dislocation.

SUMMARY

In one aspect, a removable and replaceable rigid hip orthotic is disclosed comprising a back panel configured to support a patient's lower back area; a front panel configured to support a patient's lower abdominal area that is attached to the back panel via a hinge that allows the front panel to rotate; and a leg support configured to support a patient's leg, thereby placing the hip joint in a therapeutic position. In one embodiment the leg support includes a gap or space to allow the patients leg to pass through and be received by the leg support allowing the orthotic to be removable and replaceable. The orthotic is secured to the patient with straps around the lumbar-abdominal region and around the leg supports.

In another aspect, a layer of padding is added to the inside of the orthotic between the patient and the rigid orthotic to provide cushioning. In one embodiment the padding is removable from the orthotic to allow replacement of the padding.

In certain embodiments, the straps are locked to prevent removal of the orthotic without medical supervision. In one embodiment, a Boa dial is used to lock the straps in place.

In a further embodiment, the back panel of the removable and replaceable rigid hip orthotic is provided with a pair of windows extending through the rigid panel and the padding adjacent the child. A corresponding trochanter pad is positioned within each window and arranged to bear against the region of the greater trochanter of each hip joint. An adjustment mechanism is provided that allows adjustment of the pressure applied by each trochanter pad to the hip joint. The trochanter pads thus provide anterior pressure to the joint to prevent dislocation of the femoral head.

The above described features and advantages, as well as others, will become more readily apparent to those of ordinary skill in the art by reference to the following detailed description and accompanying drawings. While it would be desirable to provide an orthotic that includes one or more of these advantageous features, the teachings disclosed herein extend to those embodiments which fall within the scope of the appended claims, regardless of whether they accomplish one or more of the above-mentioned advantages.

DETAILED DESCRIPTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
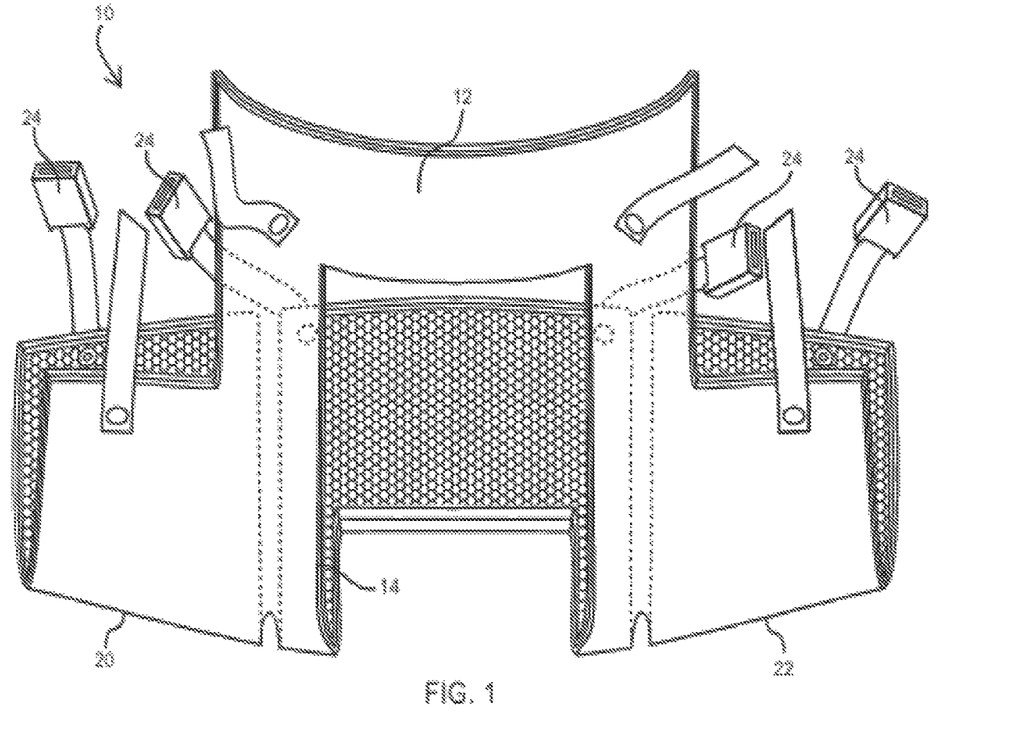
FIG. 1 is a posterior view of the orthotic.

One type of hip orthotic 10 is shown in FIG. 1. The orthotic 10 includes a back panel 12 which is molded to fit the lower back/lumbar sacral area of the patient and which contours around the patient's back and laterally to provide stability and structural integrity of the orthotic 10. The back panel 12 is formed from polypropylene or any other suitable material that is heat-formable and waterproof, but is generally rigid in construction so as to support the patient in the therapeutic position. It further includes an aperture 14 to reduce the amount of skin covered by the orthotic 10 and to allow access to the diaper area of the patient. It can be understood that the aperture 14 can be of varying size and shape but must remain limited in some respects to ensure structural stability of the orthotic 10.

Figure 2:
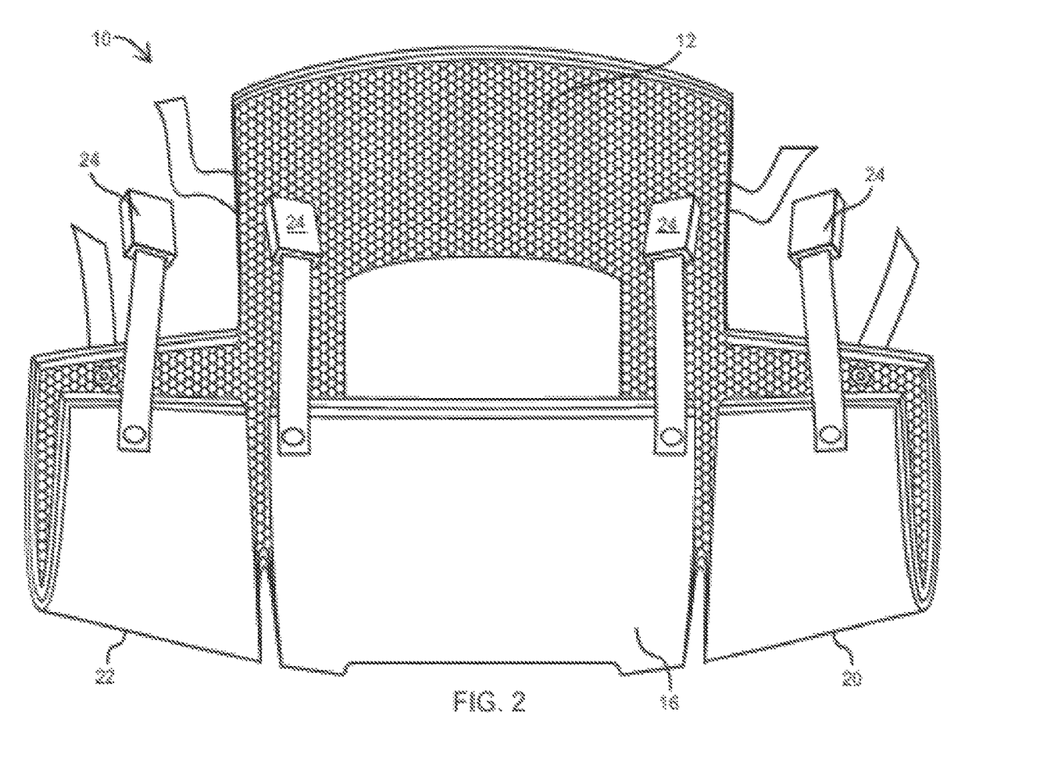
FIG. 2 is an anterior view of the orthotic shown in FIG. 1.

The orthotic 10 also includes a front panel 16 as best shown in FIG. 2. The front panel 16 can be formed from the same rigid polypropylene material as the back panel 12 and can be formed as a part of a unitary construction with the back panel 12. In one embodiment, the front panel 16 is movable with respect to the back panel 12 via a hinge 18 (best shown in FIG. 3). The hinge 18 can be any type of hinge that allows the front panel 16 to move or rotate with respect to the back panel 12. In one embodiment, the front panel 16 is scored to form the hinge 18 but other types of hinges are contemplated by this disclosure. As those with skill in the art can appreciate, the hinged front panel 16 allows the orthotic 10 to be applied and removed from the patient more easily. Additionally, the hinged front panel 16 allows for additional diaper area access if necessary.

Figure 4:
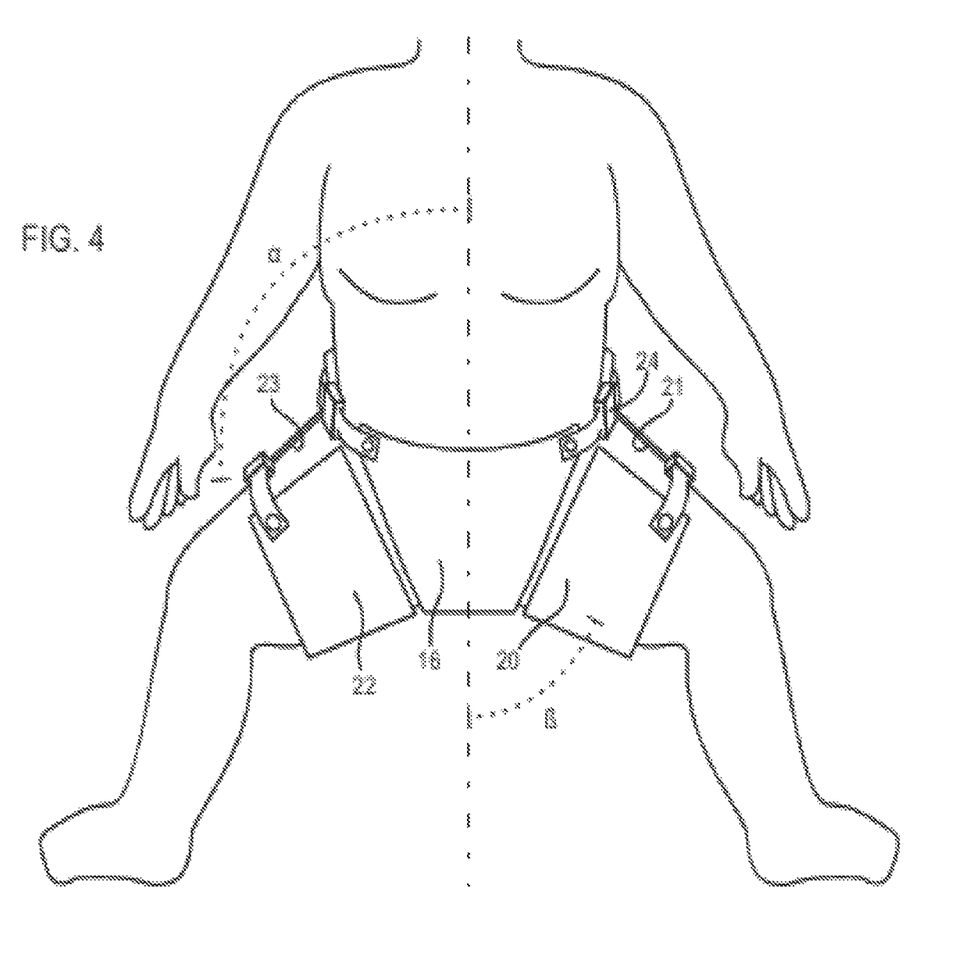
FIG. 4 is an anterior view of the orthotic shown in FIG. 1 as applied to a patient.

The orthotic 10 also includes a left leg support 20 and a right leg support 22 though it can be understood that if only one hip joint is affected by DDH, only one of the leg supports may be necessary. The leg supports 20, 22 are similarly formed out of a generally rigid material such as polypropylene, and can be formed in a unitary construction with the back panel 12 and front panel 16 as shown in one embodiment. The leg supports 20, 22 are positioned in such a way as to hold the patient's legs in the prescribed therapeutic position. The leg supports 20, 22 include openings 21, 23 which allow for the patient's legs to be moved into the orthotic 10. The openings 21, 23 are sized to allow the patient's leg to pass through into the orthotic 10. The leg supports 20, 22, when used to treat DDH, generally hold the patient's legs in a therapeutic position of which two angles are of particular importance, the angle of abduction α and the angle of flexion β. In most cases of DDH, the prescribed position is 45 degrees abduction α, and between 90 and 100 degrees flexion β as best shown in FIG. 4. It should be understood however, that this orthotic 10 can be used for various leg support angles, not just those associated with DDH.

It can be appreciated that the orthotic 10 can be either be molded to the individual patient or prefabricated in a variety of different sizes to accommodate a multitude of patients. Patients can be measured or scanned to collect size information for the orthotic 10 and then fitted with the appropriately sized orthotic 10. When the orthotic 10 is applied to the patient, the patient will not generally need to be anesthetized. The front panel 16 can be opened at the hinge 18 to accommodate placement of the orthotic 10 and the legs of the patient can pass through openings 21, 23 in the leg supports 20, 22. Once the patient is positioned in the orthotic 10, straps 24 can be used to firmly but comfortably hold the orthotic 10 in place. In one embodiment, straps 24 are used around the lumbar region, on each leg support 20, 22 and to secure the front panel 16 to the back panel 12. The straps 24 can be hook and loop fastener type, or use buckle fasteners, snaps, or any other suitable means for firmly holding the orthotic 10 in place. Such straps may also have locking features, such as a Boa dial to prevent the removal of the orthotic 10 without supervision or assistance.

Figure 3:
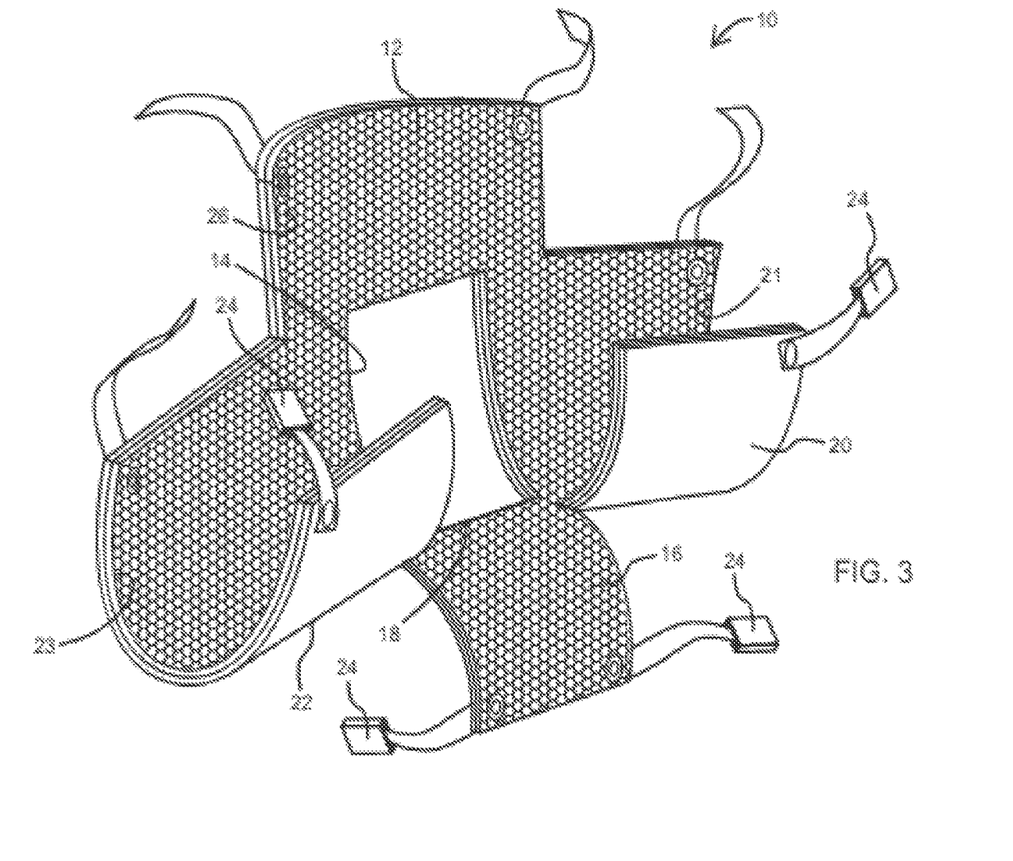
FIG. 3 is a perspective view of the orthotic shown in FIG. 1.

The orthotic 10 can also include a removable padding layer 26 as best shown in FIG. 3. The padding 26 can be a soft foam or other suitable material that can provide a barrier layer between the orthotic 10 and the patient. The padding 26 provides an element of comfort for the orthotic 10, but also increases the hygiene of the orthotic 10 as the orthotic 10 can be removed and the padding 26 either replaced or cleaned in the event of fecal/urine contamination. It can be appreciated that the padding layer 26 can reduce the discomfort of the patient and reduce skin irritations from the orthotic 10. Moreover, it can be appreciated that the orthotic 10 can be worn without the padding 26 while the patient bathes.

Figure 5:
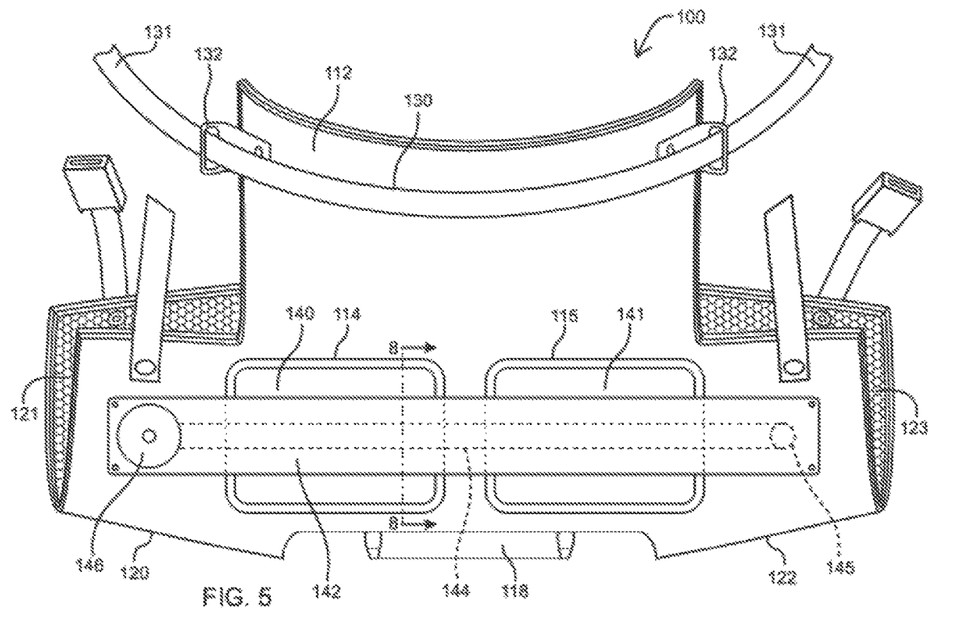
FIG. 5 is a posterior view of an orthotic according to a further embodiment.
Figure 6:
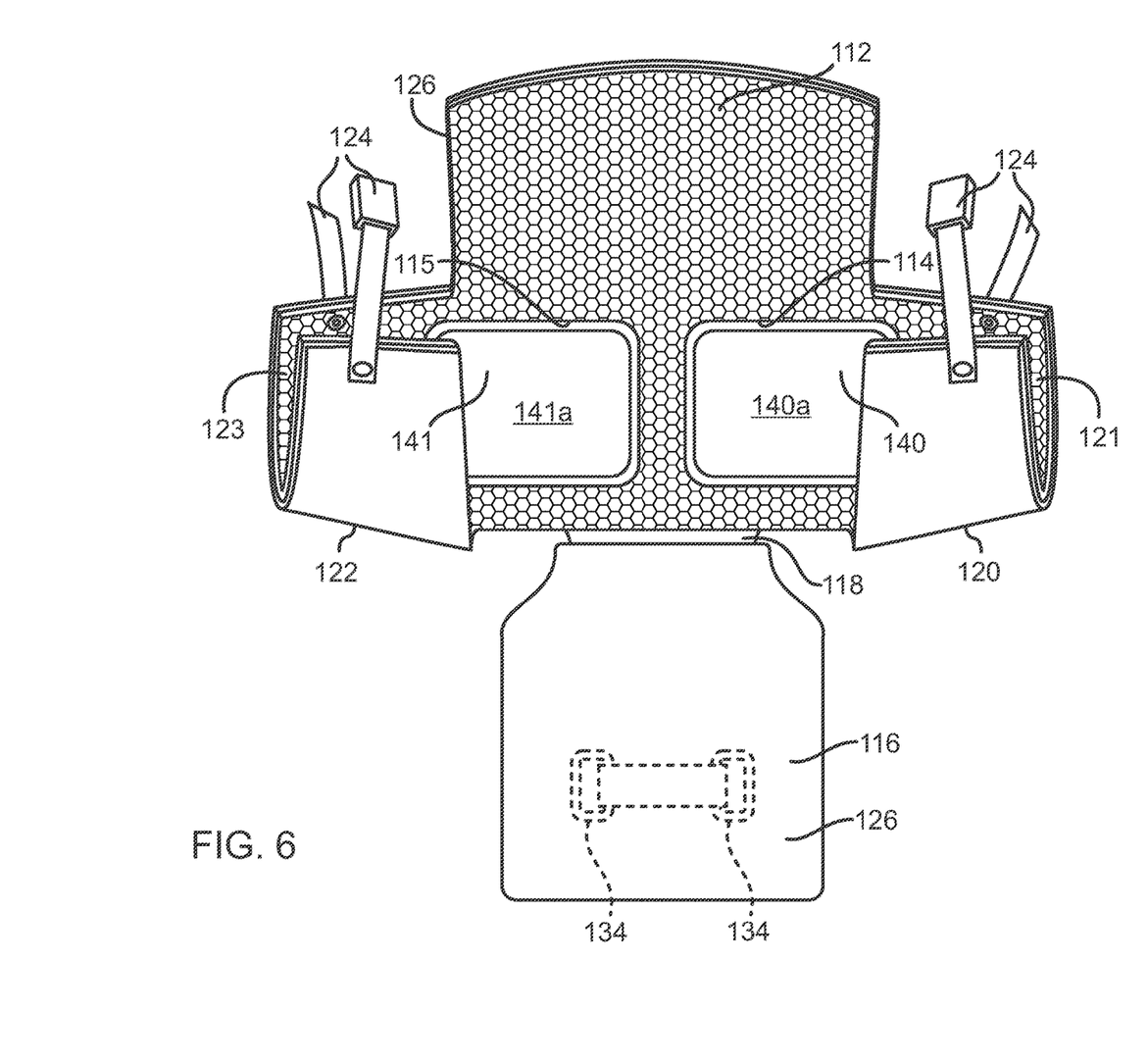
FIG. 6 is an anterior view of the orthotic shown in FIG. 5
Figures 7, 8:
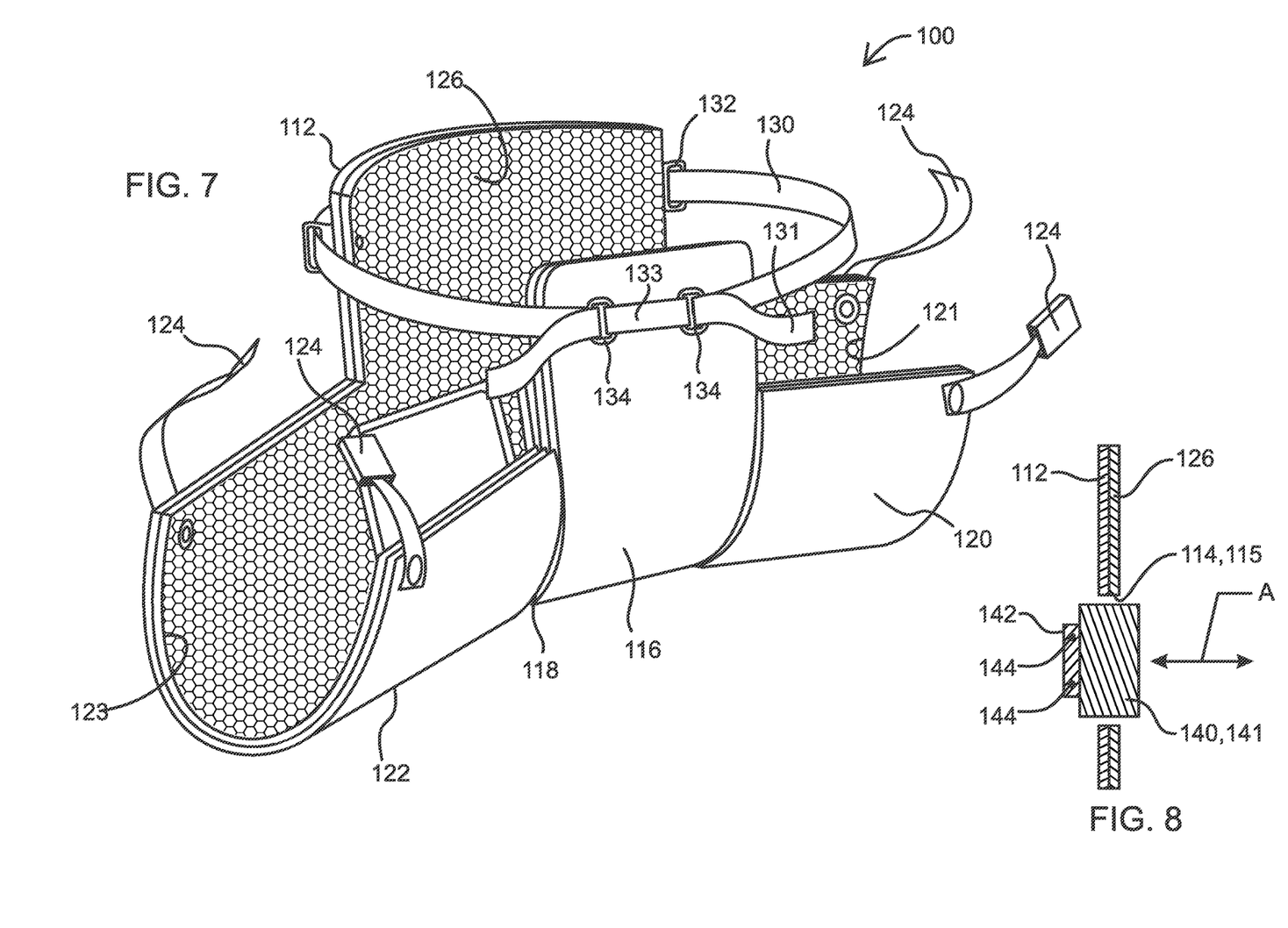
FIG. 7 is a perspective view of the orthotic shown in FIG. 5.
FIG. 8 is a cross-sectional view of the back panel of the orthotic shown in FIG. 5, taken along line 8-8.

In a further embodiment, a rigid orthotic 100 is similar in construction to the orthotic 10, as shown in FIGS. 5-7, but incorporates a feature for providing anterior pressure to the greater trochanter region of the hip joint to prevent dislocation of the femoral head. The orthotic 100 includes a back panel 112 and a front panel 116 that can be formed of the same material as the panels 12 and 16. The front panel 116 is connected to the back panel 112 by a hinge 118 that allows the front panel to be pivoted outward from the back panel, as shown in FIG. 6 and returned to wrap around the child, as shown in FIG. 7.

The rigid orthotic further includes leg supports 120, 122 similar in construction to the leg supports 20, 22, that define openings 121, 123 to receive the legs of the child. Straps 124 are provided that are similar to the straps 24 that are used to hold the child's legs within the leg supports. Like the orthotic 10, the orthotic 100 can be provided with padding 126 similar to the padding 26 so that the orthotic can be comfortably worn by the child.

The orthotic 100 incorporates a waist strap 130 that is affixed to the back panel 112 and threaded through strap guides 132 fastened to the lateral sides of the back panel, as best shown in FIG. 5. The front panel 116 includes an anchor 133 with strap guides 134 for receiving the waist strap 130. The waist strap 130 can include a releasable fastener arrangement, such as hook and loop fasteners, at the ends 131 of the strap so that the strap can be adjustably tightened onto itself after threading through the anchor strap guides 134.

The orthotic 100 further incorporates the feature for applying pressure to the greater trochanter region of the hip joint to prevent dislocation of the femoral head. In particular, a pair of trochanter pads 140, 141 are positioned within a corresponding window 114, 115 so that the inner surface 140a, 141a (FIG. 6) will bear against the hip of the child when the orthotic is in position. The orthotic 100 further provides a mechanism for adjusting the pressure applied by the trochanter pads 140, 141. In particular, the pads 140, 141 are mounted on or in contact with an adjustment strap 142 that at least spans the lateral width of the back panel 112 and preferably extends into the leg supports 120, 122. The adjustment strap 142 incorporates an adjustment mechanism in the form of a tension wire 144 extending along the length of the strap between a pulley 145 at one end and a tightening dial 146 at an opposite end of the strap. The tightening dial 146 and tensioning wire 144 can be part of a BOA™ closure sold by BOA Technology, Inc. The BOA closure may be constructed as disclosed in U.S. Pat. Nos. 7,950,112 and 7,954,204, the entire disclosures of which are incorporated herein by reference.

The dial 146 can be manually rotated to extend or retract the wire within the dial, thereby lengthening or shortening the exposed length of wire 144 within the adjustment strap 142. Shortening the exposed length of wire pushes the trochanter pads 140, 141 towards the hip joint, while lengthening the wire allows the trochanter pads to be pushed back through the windows 114, 115. In other words, the adjustment dial 146 can be rotated to move the trochanter pads 140, 141 in the direction A through the windows 114, 115 as shown in FIG. 8. In one specific embodiment, the trochanter pads 140, 141 and the adjustment strap 142 can be configured to provide two inches (2") of movement in the direction A, thereby varying the amount of pressure applied to the hip joint. Pressure sensors may be provided in the pads and/or adjustment strap to provide an indication of the amount of pressure being applied to the child's hip joint.

The trochanter pads 140, 141 can be formed of a slightly compressible material or may include a slightly compressible layer adjacent the body of the child. The material of the pads may be sufficiently compressible to adapt to the contour of the patient's anatomy at the hip joint to ensure a uniform pressure across the joint. The pads may also be provided with removable padding, like the padding on the remainder of the orthotic. The pads may be removably fastened to the adjustment strap, such as by snaps, hook-and-loop fabric or other similar components. Alternatively, the trochanter pads may be mounted to the back panel by an elastic support that allows the pads to freely move in the direction A (FIG. 8). For instance, the pads may be connected to the back panel by a flexible diaphragm fastened around the perimeter of the windows 114, 115, or by elastic straps fastened to the panel.

In the illustrated embodiment, a single adjustment strap 142 is used to simultaneously adjust the position of the trochanter pads 140, 141 and consequently the pressure applied by the pads. Alternatively, a separate adjustment strap may be provided with each separate trochanter pad, permitting separate adjustment of the pressure applied to the associated hip joint. Each adjustment strap would include its own adjustment dial 146 and associated tension wire 144 and pulley 145.

It is further contemplated that the manual adjustment dial 146 can be replaced with an electrical or electronic component that can activate the tension wire 144. For instance, the dial can be driven by a micromotor that is activated by a remote control. The trochanter pads 140, 141 and/or adjustment strap 142 can be provided with pressure sensors to sense the actual pressure being applied to the greater trochanter region of the child's hip joint. This pressure data can provide feedback to the actuation of the adjustment dial to provide a pre-determined pressure to the joint. It is further contemplated that the pressure sensor and electronic adjustment dial can work interactively to automatically adjust the dial to maintain the pre-determined pressure.

It should be understood that this disclosure is, in many respects, only illustrative. Changes may be made in details, particularly in matters of shape, and size without exceeding the scope of the invention. The invention's scope is, of course, defined in the language in which the appended claims are expressed.

What is claimed is:
1. An orthotic comprising:
   a back panel formed of a rigid material and configured to support a patient's lumbar region;
   a front panel formed of the rigid material and configured to support the patient's lower abdomen region, wherein the front panel is attached to the back panel via a hinge and the front panel is at least partially rotatable about the hinge, and wherein the front panel, when in a first position, can be secured to the back panel around the patient with at least one strap and when in a second position, can accommodate the removal and application of the orthotic to the patient; and
   at least one leg support formed of a rigid material and configured to support the patient's leg in a pre-determined position relative to the body of the patient, wherein the leg support extends from a lateral edge of the back panel and further defines an opening that extends from the back panel to an end of the leg support distal from the back panel, said opening sized and configured to receive the patient's leg therein, and wherein the at least one leg support further includes at least one strap spanning the opening for holding the patient's leg within the at least one leg support.

2. The orthotic of claim 1, wherein the orthotic further comprises a layer of padding that extends along an inside surface of the orthotic.

3. The orthotic of claim 2, wherein the padding layer is removable from the orthotic.

4. The orthotic of claim 1, wherein the back panel further comprises an aperture located generally in a patient's diaper area wherein the aperture is sized and configured to allow diapering of the patient.

5. The orthotic of claim 1, wherein each of the at least one straps include locks operable to prevent the straps from coming unsecured.

6. The orthotic of claim 1, wherein the hinge is comprised of a scored line in the rigid material.

7. The orthotic of claim 1, wherein the at least one leg support is fixed in relation to the back panel at a pre-determined angle of abduction and a pre-determined angle of flexion.

8. The orthotic of claim 7, wherein the abduction angle is 45 degrees and the flexion angle is between 90 and 100 degrees.

9. The orthotic of claim 1, further comprising:
   at least one window defined in said back panel and arranged in said back panel to be positioned at the greater trochanter region of the hip joint of the patient when the orthotic is worn by the patient;
   a pad sized to be movably disposed within said at least one window in contact with the patient's hip joint; and
   an adjustment mechanism, wherein the adjustment mechanism moves said pad relative to the back panel to apply adjustable pressure to the patient's hip joint through the pad.

10. The orthotic of claim 9, wherein the adjustment mechanism includes a strap fastened to the back panel and bearing against the pad disposed within said at least one window.

11. The orthotic of claim 10, wherein the adjustment mechanism includes a tensioning cable extending through said strap and a rotatable dial operable to increase or decrease the length of the tensioning cable within the strap to variably apply pressure to the pad.

12. The orthotic of claim 9, further comprising:
   two windows defined in said back panel, one each positioned at the greater trochanter region of a corresponding hip joint of the patient; and
   two pads, one each disposed within a corresponding one of the two windows.

13. The orthotic of claim 12, wherein the adjustment mechanism includes a strap fastened to the back panel and bearing against each pad disposed within said at least one window; and
   a tensioning cable extending through said strap and a rotatable dial operable to increase or decrease the length of the tensioning cable within the strap to variably apply pressure to the two pads.

14. A removable and replaceable pediatric hip orthotic comprising:
   an abdominal support having a front panel configured to rigidly support a patient's abdomen, and a back panel configured to rigidly support a patient's lower back and sides, wherein the front panel and back panel can be secured together with a strap when the front panel is in a first position and wherein the front panel can be moved to a second position to accommodate removal of the orthotic, further wherein the front panel is scored to allow movement between the first position and the second position; and
   at least one leg support, configured to rigidly support a patient's hip joint in a therapeutic position, wherein the leg support is attached to the back panel and includes a slot extending from the back panel to a distal end of the at least one leg support to accommodate removal and application of the orthotic.

\* \* \* \* \*